(12) United States Patent
Hopper et al.

(10) Patent No.: US 8,773,125 B2
(45) Date of Patent: Jul. 8, 2014

(54) MICROCOIL NMR FOR DOWNHOLE MICROFLUIDICS PLATFORM

(75) Inventors: Timothy Hopper, Houston, TX (US); Martin Hurlimann, Newton, MA (US); Yi-Qiao Song, Newton, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 391 days.

(21) Appl. No.: 12/981,116

(22) Filed: Dec. 29, 2010

(65) Prior Publication Data
US 2012/0169334 A1 Jul. 5, 2012

(51) Int. Cl.
*G01R 33/48* (2006.01)
(52) U.S. Cl.
USPC .............. 324/303; 324/318; 324/321
(58) Field of Classification Search
USPC ............ 324/303, 309, 318, 321; 600/411
See application file for complete search history.

(56) References Cited

U.S. PATENT DOCUMENTS

| | | |
|---|---|---|
| 3,859,851 A | 1/1975 | Urbanosky |
| 4,860,581 A | 8/1989 | Zimmerman et al. |
| 4,994,671 A | 2/1991 | Safinya et al. |
| 5,266,800 A | 11/1993 | Mullins |
| 5,684,401 A | 11/1997 | Peck et al. |
| 5,939,717 A | 8/1999 | Mullins |
| 7,141,978 B2 | 11/2006 | Peck et al. |
| 7,463,027 B2 | 12/2008 | Prammer et al. |
| 2005/0162162 A1 | 7/2005 | Itskovich et al. |
| 2008/0042650 A1 | 2/2008 | McDowell |
| 2008/0100296 A1 | 5/2008 | Massin et al. |
| 2008/0315875 A1 | 12/2008 | Sillerud |
| 2009/0216109 A1* | 8/2009 | Karmarkar et al. ........... 600/411 |
| 2009/0219019 A1* | 9/2009 | Taherian et al. .............. 324/303 |
| 2009/0256562 A1 | 10/2009 | Gao et al. |
| 2010/0156414 A1* | 6/2010 | Sakellariou et al. .......... 324/309 |

OTHER PUBLICATIONS

Peck et al., "Design and Analysis of Microcoils for NMR Spectroscopy", Journal of Magnetic Resonance Imaging, Series B, vol. 108(2), 1195, pp. 114-124.*
Burgess, et al., "Formation Testing and Sampling Through Casing", Oilfield Review, Schlumberger, Spring 2002, pp. 46-57.
Goloshevsky, et al., "Integration of biaxial planar gradient coils and an RF microcoil for NMR flow imaging", Measurement Science and Technology, vol. 16(2), 2005, pp. 505-512.
Liu, Young , "CMOS Mini Nuclear Magnetic Resonance System and its Application for Biomolecular Sensing", IEEE International Solid-State Conference, 2008, pp. 140-602.
McDowell, et al., "Operating nanoliter scale NMR microcoils in a 1 tesla field", J Magn Reson., vol. 188(1), 2007, pp. 74-82.

(Continued)

*Primary Examiner* — Melissa Koval
*Assistant Examiner* — Rishi Patel
(74) *Attorney, Agent, or Firm* — Kimberly Ballew; Darla Fonseca

(57) ABSTRACT

Methods and related apparatuses of a downhole micro nuclear magnetic resonance (NMR) device having a resonant tuning (LC) circuit for use in a formation for collecting NMR signals from a fluid in the formation while under downhole pressures and temperatures. The downhole micro NMR device includes: a micro tube for the flowing fluid to flow therethrough; at least one magnet disposed about the micro tube; and at least one micro RF coil structured and arranged approximate to the micro tube and tuned to a Larmor frequency corresponding to a applied magnetic field from the at least one magnet.

35 Claims, 10 Drawing Sheets

(56) References Cited

OTHER PUBLICATIONS

Olson, et al., "High-Resolution Microcoil 1H-NMR for Mass-Limited, Nanoliter-Volume Samples", Science Magazine, vol. 270(5244), 1995, pp. 1967-1970.

Peck, et al., "Design and Analysis of Microcoils for NMR Microscopy", Journal of Magnetic Resonance, Series B, vol. 108(2), 1995, pp. 114-124.

Seeber, et al., "Design and testing of high sensitivity microreceiver coil apparatus for nuclear magnetic resonance and imaging", Review of Scientific Instruments, vol. 72(4), 2001, pp. 2171-2179.

Sorli, et al., "Micro-spectrometer for NMR: analysis of small quantities in vitro", Measurement Science and Technology, vol. 15(5), 2004, pp. 877-880.

International Search Report and Written Opinion of the International Searching Authority of PCT International Patent Application No. PCT/US2011/049156 dated Apr. 9, 2012.

Trumbull et al. " Integrating Microfabricated Fluidic Systems and NMR Spectroscopy," IEEE Transactions on Biomedical Engineering, vol. 47, No. 1, Jan. 2000, pp. 3-7.

Wensink et al. "Measuring reaction kinetics in a lab-on-a-chip by microcoil NMR," Lab Chip, The Royal Society of Chemistry, 2005, pp. 280-284.

* cited by examiner

MICROCOIL NMR FOR DOWNHOLE MICROFLUIDICS PLATFORM

FIELD

The disclosed subject matter generally relates to downhole nuclear magnetic resonance (NMR) devices that provide measurements to determine properties of formation fluids. More particularly, relates to downhole micro NMR devices having a resonant tuning (LC) circuit that can be used in the formation for collecting NMR signals from the formation fluid in the formation, while under downhole pressures and temperatures.

BACKGROUND

Nuclear Magnetic Resonance (NMR) measurements of oil properties have been used to aide in reservoir fluid characterization since the early 1950s. Today, the detailed knowledge of fluid composition is a key ingredient for successful management of oilfield reservoirs. The oil composition determines the Pressure-Volume-Temperature (PVT) behavior. Viscosity measurements in addition to the T1, T2, diffusion, chain length, chemical structure, emulsion, waxing, and phase transition are all important fluid properties. Viscosity can be used as a fingerprint for other reservoir properties, such as compartmentalization. Compartmentalization is the situation in which some reservoirs have multiple levels of 'pay zones' and these may or may not be hydraulically connected. This has implications for the production and completions design and execution. During production there can be asphaltene drop-out or waxing problems that can cause loss of production. It is highly desirable to measure fluid properties under downhole conditions since many properties depend critically on temperature and pressure. It is also well understood that samples can undergo irreversible changes as they are extracted from the formation and transferred to the laboratory.

There are various downhole tools such as the MDT and the CHDT (trademarks of Schlumberger) tools that can be useful in obtaining and analyzing fluid samples. The downhole tools such as the MDT tool (see, e.g., U.S. Pat. No. 3,859,851 to Urbanosky, and U.S. Pat. No. 4,860,581 to Zimmerman et al., which are hereby incorporated by reference herein in their entireties) typically include a fluid entry port or tubular probe cooperatively arranged within wall-engaging packers for isolating the port or probe from the borehole fluids. It is noted they also include sample chambers which can be coupled to the fluid entry by a flow line having control valves arranged therein.

Regarding NMR measurements, the fluid sample is located in a static magnetic field and exposed to resonant frequencies (RF) pulses. The generated RF signal, produced by the irradiating RF pulses to the fluid sample, is then recorded. Depending on the exact configuration of the static field and the details of the RF pulses that are applied to the sample, many different measurements can be implemented. With uniform static fields, NMR spectra can be recorded that give information on the chemical composition of the fluids. If the static field is made non-uniform, either by applying a static field that is spatially non-uniform or by applying pulsed gradient fields, NMR imaging, diffusion and flow measurements become possible. In all cases, relaxation measurements can also be performed.

SUMMARY

The present disclosed subject matter relates to a downhole micro nuclear magnetic resonance (NMR) device having a resonant tuning (LC) circuit for use in a formation for collecting NMR signals from a fluid in the formation while under downhole pressures and temperatures. The downhole micro NMR device includes: a micro tube for the flowing fluid to flow therethrough; at least one magnet disposed about the micro tube; and at least one micro RF coil structured and arranged approximate to the micro tube and tuned to a Larmor frequency corresponding to a applied magnetic field from the at least one magnet.

According to aspects of the subject matter disclosed, the at least one magnet can include angled poles that create a gradient of the applied magnetic field along a direction of flow of the fluid in the micro tube based upon the micro NMR device being powered between 100 nW to 5 W. The at least one magnet can be structured and arranged to provide for a homogeneous static field that allows for detection of NMR spectroscopy measurements based upon the micro NMR device being powered between 100 nW to 5 W. The at least one magnet can be structured and arranged to provide for a gradient field that allows for detection of NMR diffusion measurements based upon the micro NMR device being powered between 100 nW to 5 W. The at least one magnet can be one of a single magnet or two or more magnets, that includes one of a non uniform shaped or multiple non uniform shape pole pieces, that provides for at least two distinct regions of substantially different magnetic field strengths to allow detection of NMR measurements based upon the micro NMR device being powered between 100 nW to 5 W. The at least one magnet can be at least two magnets that are arranged to provide for spatially separate magnetic fields, each having substantially different magnetic field strengths, to allow detection of NMR asphaltene measurements based upon the micro NMR device being powered between 100 nW to 5 W.

According to aspects of the subject matter disclosed, the downhole pressure can be greater than 50 psi and the formation temperature can be greater than 50 Celsius. The micro NMR device can be a NMR probe that is controlled by a spectrometer and powered by a power supply. The power used to power the micro NMR device can be one of less than 1 mW, less than 30 mW, less than 50 mW, less than 75 mW, between 90 nW to 2.5 W or between 100 nW to 5 W. The at least one micro RF coil can be from a metal or an alloy such as one of copper, gold or silver. The NMR device can further comprise of an inductor that is fixed and placed in series with the LC circuit to reduce a capacitance. The LC circuit can be constructed of non-magnetic material and capable of tuning the micro NMR device.

According to aspects of the subject matter disclosed, the at least one micro RF coil can be at least two micro RF coils structured and arranged approximate the micro tube, each micro RF coil is at spatially separate locations and tuned to different local resonant frequencies. The two or more micro RF coils are structured and arranged to have each micro RF coil electrical inductance that is electrically decoupled from each other. The micro NMR device is capable of making at least two NMR measurements at one of different field strengths, different gradient strengths, or both. It is possible the field strengths can be between 0.04 to 2 T or 0.1 to 2 T or more. The gradient strengths can be one of a static gradient or pulsed gradient that provide for multiple diffusion measurements. The multiple diffusion measurements can be provided by a pulse program such as a Diffusion Editing (DE) sequence or other diffusion sequences that are well known to the experts in the field. Further, the NMR device may comprise of one or more coil shielding device. The micro RF coil can be a solenoid-shaped coil encompassing a volume within the micro tube. The micro RF coil can be fabricated on the micro tube. The micro RF coil can be a spiral, substantially planar coil. The micro RF coil can further comprise of one or more gradient coils.

According to aspects of the subject matter disclosed, the LC circuit can include one or more capacitor, the one or more capacitor is one of a variable capacitor or a fixed capacitor. The micro tube can have an approximate diameter from 100 microns to about 5 millimeters. The micro tube can have an approximate length of less than 50 mm, less than 25 mm, less than 10 mm or from 0.1 mm to about 1 meter or more. The micro tube can comprise of a capillary tube. The micro tube may comprise of a substrate having a passageway therethrough, wherein the substrate may comprise of at least two pieces that are attached together to form the passageway. It is possible the passageway, channel or tube can be a unitary device not made from two pieces. The substrate can be made from one of sapphire, silica or quartz, electrically insulated and dielectric. The NMR device can further comprise of a fluid delivery system in fluid communication with the micro tube and an oilfield related tool such as a downhole tool.

According to aspects of the subject matter disclosed, the at least one magnet can be an array of magnets, the array of magnets are of a size larger than a size of the micro tube. The at least one magnet is a permanent magnet, a superconducting electromagnet, or a non-superconducting electromagnet. The micro tube comprises a substrate having a passageway therethrough and the at least one magnet is disposed on the substrate. The NMR device can further comprise of a permeable magnetic material. Wherein at least a portion of the micro NMR device can be constructed on one of a substrate or a chip using micro fabrication techniques. The micro NMR device can be positioned within a oilfield application tool, a downhole fluid sampling tool or a device capable of operating in a subterranean environment such as a formation under formation pressures and temperatures.

In accordance with another embodiment of the disclosed subject matter, a method for making a downhole nuclear magnetic resonance (NMR) measurement on a fluid in a formation using a NMR device having a resonant tuning (LC) circuit. The method includes: (a) flowing the fluid from a downhole tool into a micro tube of the NMR device having a static magnetic field, wherein the NMR device includes at least one magnet disposed about the micro tube and at least one micro RF coil structured and arranged approximate to the micro tube and tuned to a Larmor frequency corresponding to a applied magnetic field from the at least one magnet; (b) applying RF magnetic field pulses to the fluid; (c) detecting magnetic resonance signals from the fluid; (d) analyzing the detected magnetic resonance signals to extract information about the fluid such as an NMR measurement such as one of a spectroscopy measurement, diffusion measurement, a relaxation measurement or a combination thereof.

According to aspects of the subject matter disclosed, the applied magnetic field can be a homogeneous static field allows for detection of NMR spectroscopy measurements based upon the micro NMR device being powered between 100 nW to 5 W. The applied magnetic field provide for a gradient field that allows for detection of NMR diffusion measurements based upon the micro NMR device being powered between 100 nW to 5 W. The at least one magnet can be one of a single magnet or two magnets, that have one of a non uniform shaped or include multiple pole pieces that are not uniform, to provide for at least two distinct regions of substantially different magnetic field strengths to allow detection of NMR measurements based upon the micro NMR device being powered between 100 nW to 5 W. The at least one magnet can be at least two magnets that are arranged to provide for spatially separate magnetic fields, each having substantially different magnetic field strengths, to allow detection of NMR asphaltene measurements based upon the micro NMR device being powered between 100 nW to 5 W. Wherein the powering of the micro NMR device can be one of less than 1 mW or between 100 nW to 5 W.

According to aspects of the subject matter disclosed, the method further comprises an inductor that can be fixed and placed in series with the LC circuit to reduce a capacitance. The at least one micro RF coil can be at least two micro RF coils structured and arranged approximate to the micro tube, each micro RF coil is at spatially separate locations and tuned to different local resonant frequencies. The micro NMR device can be capable of making at least two NMR measurements at one of: (a) different field strengths between 0.04 to 2 T or 0.1 to 2 T or more; (b) different gradient strengths that are one of a static gradient or pulsed gradient, or (c) both. It is conceivable that the multiple diffusion measurement can be with a single gradient strength, for example, by using different timings.

According to aspects of the subject matter disclosed, the LC circuit can include one or more capacitor, the one or more capacitor is one of a variable capacitor or a fixed capacitor. The micro tube comprises a substrate having a passageway therethrough, the substrate comprises of one of a single unitary device or at least two pieces that are attached together to form the passageway. The substrate can be dielectric, electrically insulating made from glass, made from quartz, or made from one of silica or sapphire.

In accordance with another embodiment of the disclosed subject matter, a A downhole micro nuclear magnetic resonance (NMR) device having a resonant tuning (LC) circuit for use in a formation for collecting NMR signals from a fluid in the formation for measuring properties of the formation fluids. The micro NMR device including: a micro channel for providing flowing fluid to flow therethrough and for conducting downhole NMR measurements, the micro channel is capable of operating under formation pressures and temperatures; at least one magnet disposed about the micro channel having magnet portions, each magnet portion has a magnetic polarizing field direction that encapsulates at least one portion of the micro channel to provide for a static magnetic field, each magnet portion has a different static magnetic field strength; at least one micro RF coil structured and arranged approximate to the micro tube and operatively configured to generate RF magnetic fields in at least one portion of the micro channel tuned to a Larmor frequency corresponding to the applied static magnetic field from at least one portion of the magnet portions of the at least one magnet; at least one micro receiver for receiving the NMR measurement signals; and a processor in communication with the at least one receiver stores the NMR measurement signals and analyzes the received NMR measurement signals to measure properties of the formation fluids based upon the micro NMR device being powered by a power source having a power less than 1 mW or between 100 nW to 5 W.

Further features and advantages of the disclosed subject matter will become more readily apparent from the following detailed description when taken in conjunction with the accompanying Drawing.

BRIEF DESCRIPTION OF THE DRAWINGS

The present disclosed subject matter is further described in the detailed description which follows, in reference to the noted plurality of drawings by way of non-limiting examples of exemplary embodiments of the present disclosed subject matter, in which like reference numerals represent similar parts throughout the several views of the drawings, and wherein.

DETAILED DESCRIPTION OF THE PREFERRED EMBODIMENTS

Figure 1:
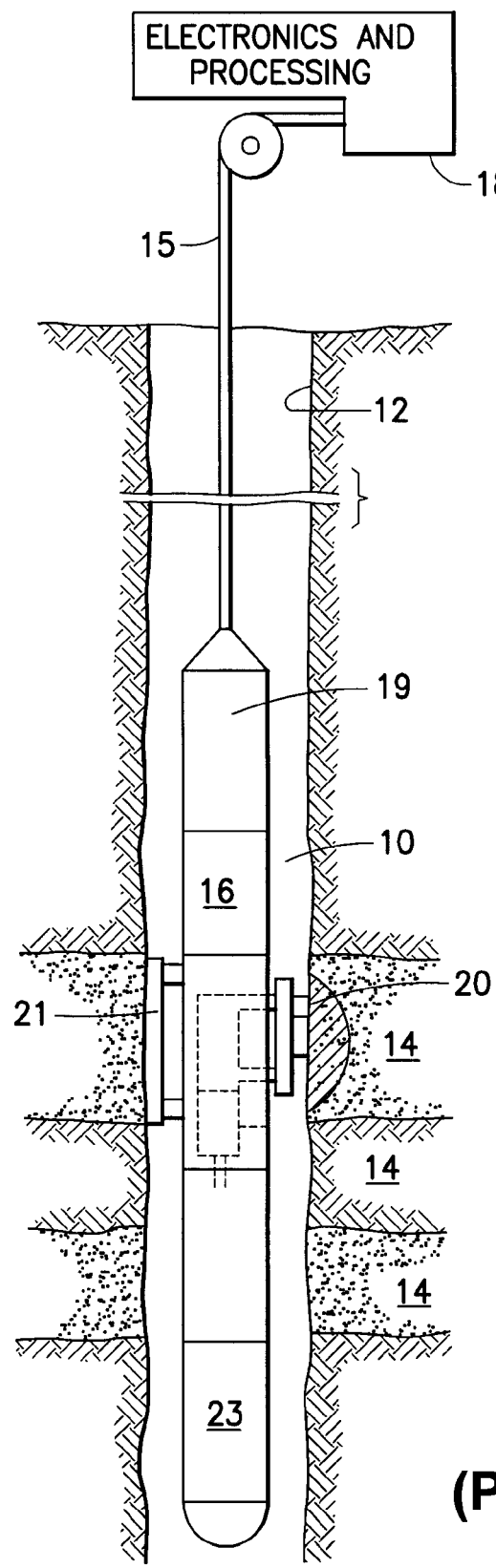
FIG. 1 shows a prior art schematic diagram showing a downhole/borehole tool with an sampling port.

The particulars shown herein are by way of example and for purposes of illustrative discussion of the embodiments of the present disclosed subject matter only and are presented in the cause of providing what is believed to be the most useful and readily understood description of the principles and conceptual aspects of the present disclosed subject matter. In this regard, no attempt is made to show structural details of the present disclosed subject matter in more detail than is necessary for the fundamental understanding of the present disclosed subject matter, the description taken with the drawings making apparent to those skilled in the art how the several forms of the present disclosed subject matter may be embodied in practice. Further, like reference numbers and designations in the various drawings indicated like elements.

Overview

The present disclosed subject matter relates to methods and related apparatuses of a downhole micro nuclear magnetic resonance (NMR) device having a resonant tuning (LC) circuit for use in a formation for collecting NMR signals from a fluid in the formation while under downhole pressures and temperatures. The downhole micro NMR device includes: a micro tube for the flowing fluid to flow therethrough; at least one magnet disposed about the micro tube; and at least one micro RF coil structured and arranged approximate to the micro tube and tuned to a Larmor frequency corresponding to a applied magnetic field from the at least one magnet At least one embodiment of the disclosed subject matter utilizes a NMR device having a micro coil NMR probe, and a thin capillary tube, that is placed inside a magnet system. The NMR device can be controlled and powered by a spectrometer and power supply. The micro coil can consists of copper wire wound around the capillary tube, or other materials may be used in the creating the coil. The LC circuit is used to tune the probe and may be constructed using non-magnetic components. It is possible the RF coil includes one or more capacitors, wherein the capacitor(s) may be one of variable or fixed capacitors. Further, it is also possible to include an inductor that can be placed in series with the RF coil.

The measurement of diffusion and relaxation distribution functions (D-T2) has proven to be a valuable tool for identifying and quantifying different fluids in the formation. It is noted that current uses of D-T2 maps from in-situ formation measurements have been obtained using downhole tools, by non-limiting example, wireline and drilling-while-measuring tools. These tools measure the oil in the formation and are influenced by the rock wettability and magnetic susceptibility differences. Having an ex-situ NMR measurement at downhole pressure and temperature offers the possibility of true fluid characterization as well as helping to determine formation wettability (by comparison to the in-situ measurement).

Regarding the downhole tools and methods which expedite the sampling of formation fluids, the downhole tools, i.e., sampling tools, are utilized to carry downhole the NMR device(s) of the subject matter disclosed in this application. By way of example and not limitation, tools such as the previously described MDT tool of Schlumberger (see, e.g., previously incorporated U.S. Pat. No. 3,859,851 to Urbanosky, and U.S. Pat. No. 4,860,581 to Zimmerman et al.) with or without OFA, CFA or LFA module (see, e.g., previously incorporated U.S. Pat. No. 4,994,671 to Safinya et al., U.S. Pat. No. 5,266,800 to Mullin, U.S. Pat. No. 5,939,717 to Mullins), or the CHDT tool (see, e.g., previously incorporated "Formation Testing and Sampling through Casing", Oilfield Review, Spring 2002) may be utilized. An example of a tool having the basic elements to implement the invention is seen in schematic in FIG. 1.

The subject matter disclosed in the application discloses devices and methods using collected downhole fluids and measuring properties of the formation fluid effectively in downhole tools. The formation fluid maybe a gas, a liquid or some combination thereof, transferred from a sample bottle (MPSR) in Schlumberger MRMS Module of the Modular Dynamics Tester (MDT) as noted above to the NMR device. Further, the devices, apparatuses and methods can provide for NMR measurements while in the formation under formation pressures and temperatures. It is note an NMR device can measure and characterize single phase and multi-phase fluids. Further, the NMR device can provide a method for obtaining complex chemical structures of molecular compositions as well as bulk relaxation and diffusion measurements. With homogeneous magnetic fields spectroscopic information can be acquired that can then be used to determine the fluid properties of the sample.

At least one aspect of the disclosed subject matter is that it can, among other things and by-non-limiting example, overcome some of the known issues. NMR is intrinsically a relatively insensitive technique and successful implementation requires careful consideration of the signal-to-noise ratio (SNR) of the measurement. For example, SNR can be increased by using the highest available magnetic fields and the largest possible sample. However, difficulties with this approach include: (i) it is hard to generate large magnetic fields with the required homogeneity over the whole sample; (ii) requires high power rf amplifiers to generate the required excitation pulses across the whole sample; (iii) in many cases, it is difficult to obtain a large enough sample (e.g. biological sample). If the sample does not fill the whole sample, the filling factor decreases and SNR of the measurement becomes too low.

According to some aspects of the disclosed subject matter, it is possible to build a magnet system with varying field strength, such that at two spatially separated locations you can have different coils tuned to the local resonant frequencies. Thus enabling multiple NMR measurements at different field strengths. Each location may or may not have different gradient strengths. This is ideally suited for a flow line type of measurement in which multiple sensors (not necessarily NMR) can be used to make noninvasive measurements on the fluid sample.

Further, the gradient strengths could be static or pulsed gradients that enable us to obtain multiple diffusion measurements. These diffusion measurements may also be achieved through innovative pulse programs such as a Diffusion Editing (DE) sequence.

According to some aspects of the disclosed subject matter, can include a microcoil Nuclear Magnetic Resonance (NMR) system that is embedded into a microfluidics system. This module is designed to fit into a downhole fluid sampling tool such as, but not limited to, a MDT sample chamber (MRSC), as noted above. This module will be able to provide NMR data on oil flowing through the fluid sampling tool (may be fluid not flowing), specifically to provide the T1, T2, and T1/T2 ratio measurements, D-T2 measurements, and split 180 degree measurements that can all be used to infer oil composition as well as detect and quantify the presence of asphaltenes.

At least one other aspect of the disclosed subject matter, among other things and by non-limiting example, the disclosed NMR device can provide downhole NMR measurements on pure oil samples, which will provide fluid characterization of the sample in real time.

Discussion of the Disclosed Subject Matter

FIG. 1 shows a borehole logging tool 10 for testing earth formations and optionally analyzing the composition of fluids from the formation 14 in accord with invention is seen. As illustrated, the tool 10 is suspended in the borehole 12 from the lower end of a typical multiconductor cable 15 that is spooled in the usual fashion on a suitable winch (not shown) on the formation surface. On the surface, the cable 15 is electrically connected to an electrical control system 18. The tool 10 includes an elongated body 19 which encloses the downhole portion of the tool control system 16. The elongated body 19 carries a probe 20 and an anchoring member 21 and/or packers (not shown in FIG. 1). The probe 20 is preferably selectively extendible as is the anchoring member 21 and they are respectively arranged on opposite sides of the body. The probe 20 is equipped for selectively sealing off or isolating selected portions of the wall of borehole 12 such that pressure or fluid communication with the adjacent earth formation is established. Also included with tool 10 is a fluid collecting chamber block 23. It is noted that the fluid may be flowing or not flowing at the time of the NMR measurement.

Figure 2:
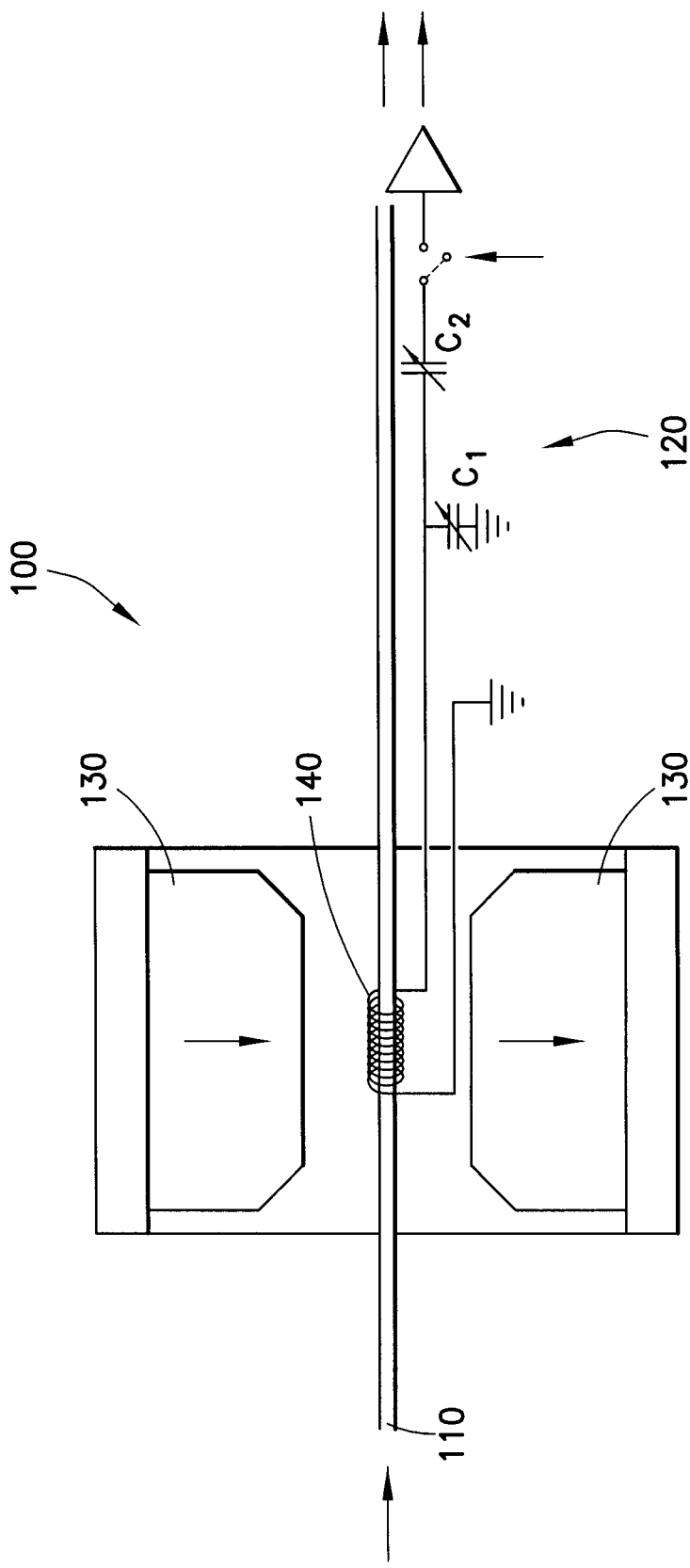
FIG. 2 shows the NMR device 100 includes a micro tube (or channel) 110, a resonant tuning (LC) circuit 120, at least one magnet 130 and at least one micro RF coil (or probe) 140, according to embodiments of the disclosed subject matter.

FIG. 2 shows at least one NMR device according to the disclosed subject matter. The NMR device 100 includes a micro tube (the tube may be considered a channel) 110, a resonant tuning (LC) circuit 120, a magnet 130 and a micro RF coil (or probe) 140. The micro RF coil 140 can be structured and arranged to be approximate to the micro tube 110 and tuned to a Larmor frequency corresponding to an applied magnetic field from the magnet 130. It is noted that NMR device 100 may be constructed using micro-fabrication techniques. Further, a fluid delivery system (not shown) is in fluid communication with the micro tube 110 and an oilfield related tool (not shown) such as a downhole tool, noted above. It is also conceived that the NMR device 100 further includes one or more coil shielding device. Shielding of the NMR probe from electrical noise can be achieved by using, but not limited to, a copper can or copper wire mesh. Ground of the components is also an essential part of minimizing noise in the coil. The spectrometer and power supply should ideally also be RF shielded. Further, the micro RF coil 140 can be made from a metal or an alloy such as one of copper, gold or silver.

Figure 3A:
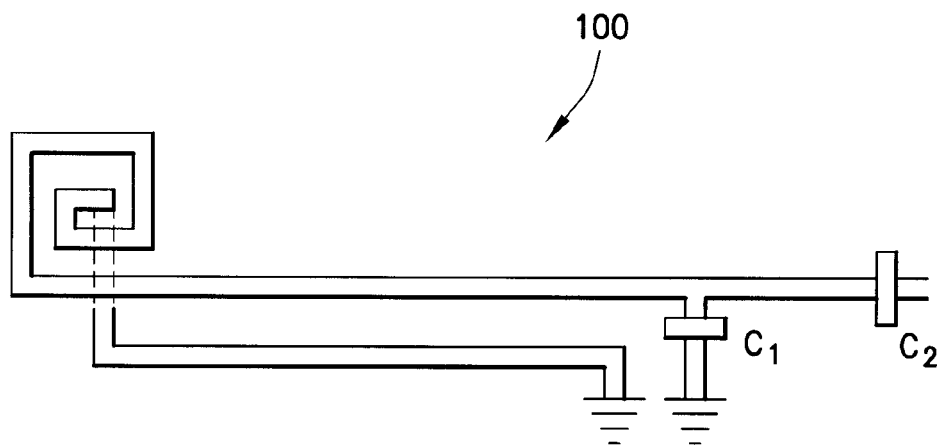
FIG. 3A shows the NMR device 100 having the micro RF coil and LC circuit embedded in a glass etched channel used for microfluidic applications, according to embodiments of the disclosed subject matter.
Figure 3B:
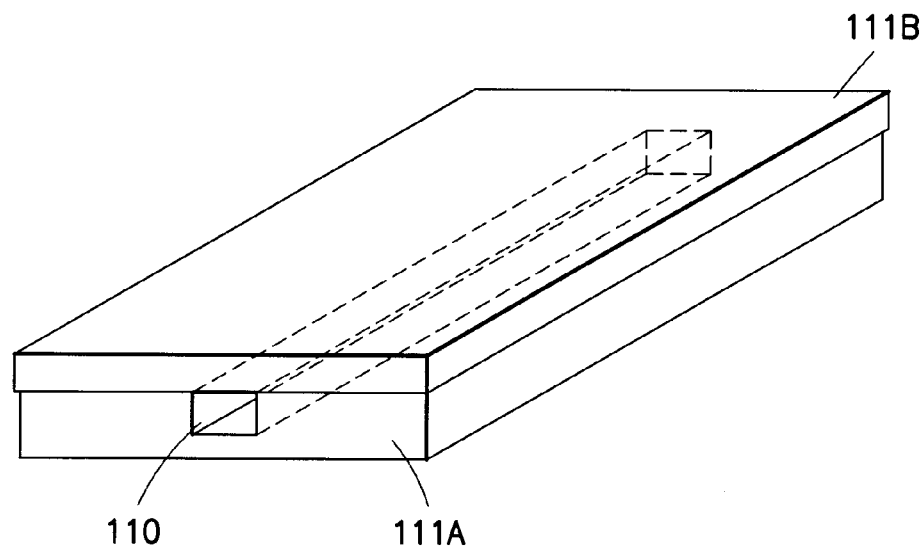
FIG. 3B shows the micro tube or channel 110 can comprise a substrate having a passageway therethrough, wherein the substrate comprises at least two pieces 111A and 111B that are attached together to form the passageway (tube, channel, passageway) 110, according to embodiments of the disclosed subject matter.

Referring to FIGS. 3A and 3B, FIG. 3A shows the micro RF coil 140 and LC circuit 120 can be embedded in a glass etched channel 110 used for microfluidic applications. These systems can be designed and fabricated in large quantities using known micromachining methods. Some of the methods include: film deposition processes, such as spin coating and chemical vapor deposition, laser machining or photolithographic techniques, e.g., UV or X-ray processes, etching methods which may be performed by either wet chemical processes or plasma processes LIGA processing and plastic molding. FIG. 3B shows the micro tube 110 can comprise a substrate having a passageway therethrough, wherein the substrate comprises at least two pieces 111A and 111B that are attached together to form the passageway. It is noted that the substrate can be made from one of sapphire, silica or quartz, electrically insulated and dielectric. Further, it is also possible the substrate could comprise of non-conductive material such as glass, ceramic, a polymer or some combination thereof. The micro tube (or micro channel) 110 can have an approximate diameter from 100 microns to about 5 millimeters. Further, the micro tube 100 can have an approximate length of less than 10 mm, less than 25 mm, less than 50 mm or from 0.1 mm to about 1 meter or more. Further still, at least a portion or all of the micro NMR device can be constructed on one of a substrate or a chip using micro fabrication techniques.

Figure 4:
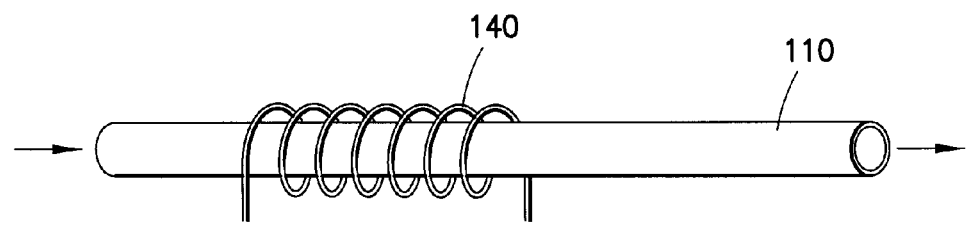
FIG. 4 shows the micro RF coil 140 that can be a solenoid wound around a capillary tube 110, such as, but limited to, a sapphire capillary tube, according to embodiments of the disclosed subject matter.

FIG. 4 shows the micro RF coil 140 that can also be a solenoid wound around a capillary tube, such as, but limited to, a sapphire capillary tube. The sapphire capillary tubes have been successfully tested in our lab up to 20,000 psi approximately, by non-limiting example. Downhole analysis of the oil must occur at formation pressures and temperatures, and hence it is important to have a capillary or substrate system that can handle these large pressures and temperatures. For example, the downhole pressure can be greater than 50 psi and the formation temperature can be greater than 50 Celsius. Generally, it is possible to use multiple coils in series (flow) or in parallel, wherein these coils could be located in different $B_o$ field strengths and/or gradient strengths. This may allow for spatially imaging the flow of the fluid and see how its properties change along a flow path if it is a multiphase mixture. Further, the use of multiple coils in different locations and different gradients can provide diffusion measurements to separate fluid types.

Figure 5:
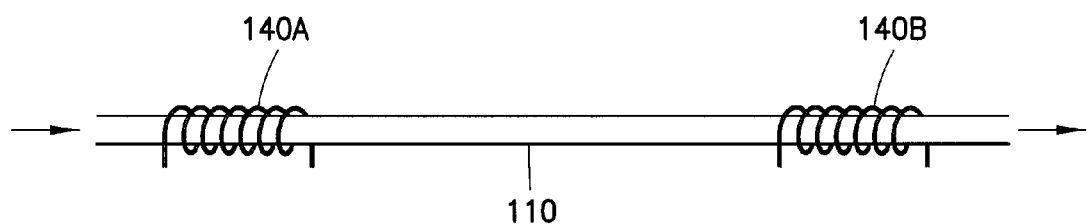
FIG. 5 shows the micro RF coil 140 may also have at least two micro RF coils 140A and 140B structured and arranged approximate the micro tube 110, each micro RF coil 140 can be at spatially separate locations and tuned to different local resonant frequencies, according to embodiments of the disclosed subject matter.

FIG. 5 shows the micro RF coil 140 may also have at least two micro RF coils and 140B structured and arranged approximate the micro tube 110, each micro RF coil 140 can be at spatially separate locations and tuned to different local resonant frequencies. Further still, the two or more micro RF coils can be structured and arranged to have each micro RF coil electrical inductance that is electrically decoupled from each other. Thus, the micro NMR device 100 can be capable of making at least two NMR measurements at one of different field strengths, different gradient strengths, or both. It is noted that the field strengths can be between 0.04 to 2 T or 0.1 to 2 T or more and the gradient strengths can be one of a static gradient or pulsed gradient, which can provide for multiple diffusion measurements. For example, the multiple diffusion measurements may be provided by a pulse program such as a Diffusion Editing (DE) sequence.

Figure 6:
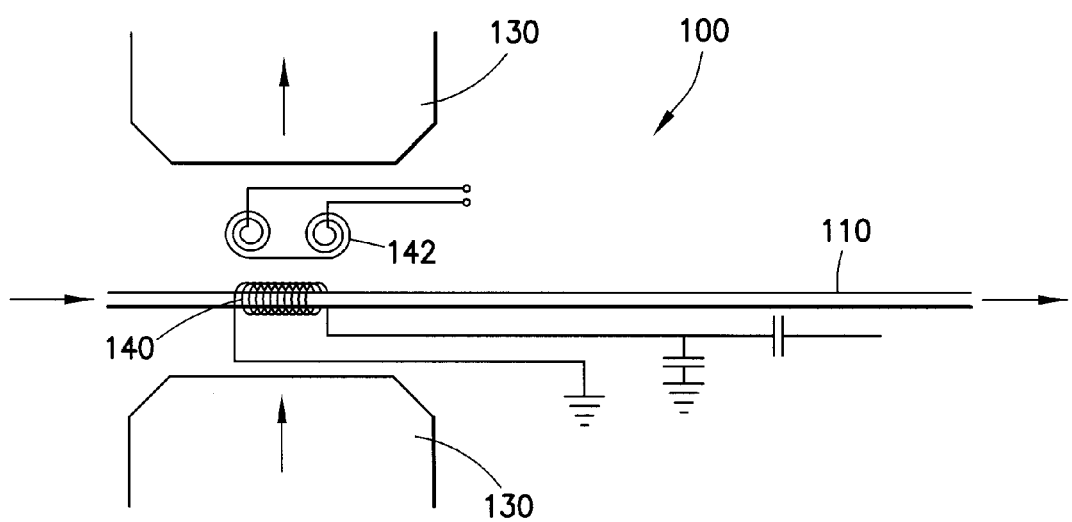
FIG. 6 shows the NMR device 100 optionally including one or more gradient coils 142 which may be constructed using micro-fabrication techniques, including electroplating technology, according to embodiments of the disclosed subject matter.

FIG. 6 shows the NMR device 100 may optionally include one or more gradient coils 142 which may also be constructed using micro-fabrication techniques, including electroplating technology. Further, the micro-fabrication techniques can be effective in establishing accurate geometries and structural stability for the downhole tool components. It is conceived that the NMR device 100 components noted above may be one of micro or macro sized.

Figure 7:
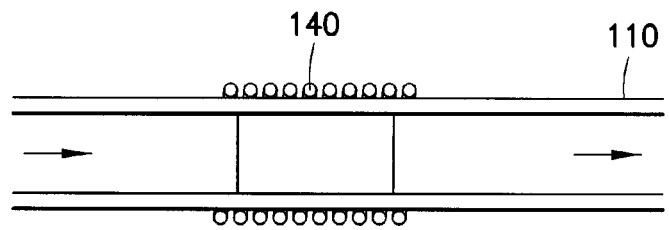
FIG. 7 shows the micro RF coil 140 can be a solenoid-shaped coil encompassing a volume within the micro tube 110, according to embodiments of the disclosed subject matter.

FIG. 7 shows the micro RF coil 140 can be a solenoid-shaped coil encompassing a volume within the micro tube 110. It is possible the micro RF coil 140 can be fabricated on the micro tube 110. The micro RF coil may be shaped in a spiral that is a substantially planar coil.

The micro RF coil 140 (see FIGS. 2, 4, 5, 7) can be small, such that the NMR sensitive area/region can also be small and variation of the static magnetic field inhomogeneity will likely be small over this region. It is noted, that it is possible to make NMR measurements using the micro NMR device 100 even though the static magnetic field can be non-homogeneous when considered over larger dimensions or areas. Because the electrical power required to excite the NMR spins with the micro RF coil 140 is relatively small, a miniaturized magnetic resonance spectrometer (not shown) can be structured. Further, the power used to power the micro NMR device 100 can be one of less than 1 mW, less than 30 mW, less than 50 mW, less than 75 mW, less than 100 mW, between 90 nW to 1.5 W, between 90 nW to 2.5 W or between 100 nW to 5 W. It is noted that the peak power can be less than 1 W, and the average power may be, by non-limiting example, in the mW range, however, other configurations are possible. Further, the power supply can either come from the downhole tool, i.e., wireline tool string power supply or from a battery situated near the assembly and/or device. Further, it is noted that to keep the magnet field as strong as possible, the fluid being sampled should be as close to the magnet(s) as possible and that the magnetic field be as homogenous as can be, view of the downhole issues, i.e., design of the device, downhole environmental issues such as temperature.

Figure 8:
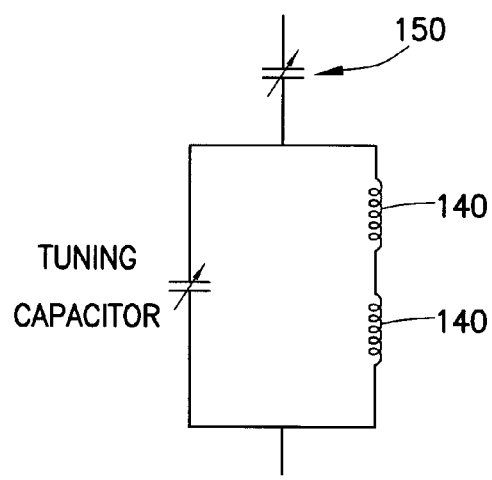
FIG. 8 shows the NMR device 100 optionally having an inductor 150 fixed and placed in series with the LC circuit 120 to reduce a capacitance, according to embodiments of the disclosed subject matter.

FIG. 8 shows the NMR device 100 optionally having an inductor 150 fixed and placed in series with the LC circuit 120 to reduce a capacitance. It is possible the LC circuit 120 can be constructed of non-magnetic material and capable of tuning the micro NMR device 100.

Figure 9:
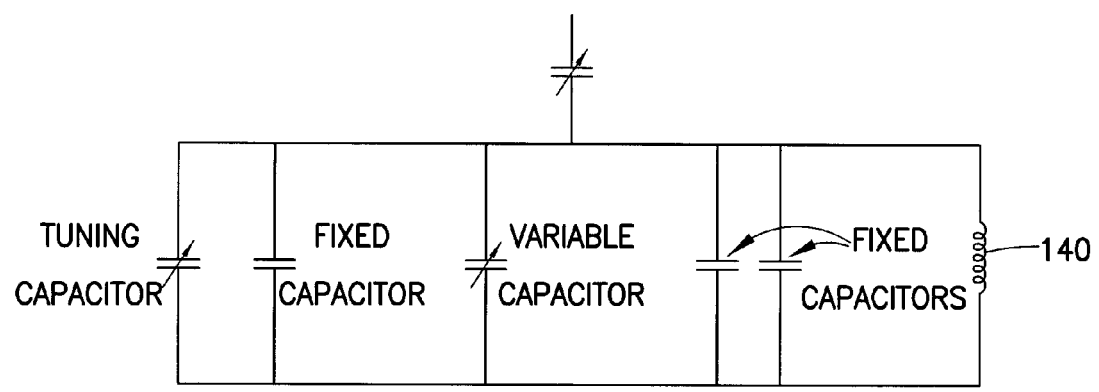
FIG. 9 shows the NMR device 100 optionally having the LC circuit 120 including one or more capacitor 122, wherein the one or more capacitor 122 can be one of a variable capacitor 122a or a fixed capacitor 122b, according to embodiments of the disclosed subject matter.

FIG. 9 shows the NMR device 100 optionally having the LC circuit 120 including one or more capacitor 122, wherein the one or more capacitor 122 can be one of a variable capacitor 122a or a fixed capacitor 122b.

Figure 10:
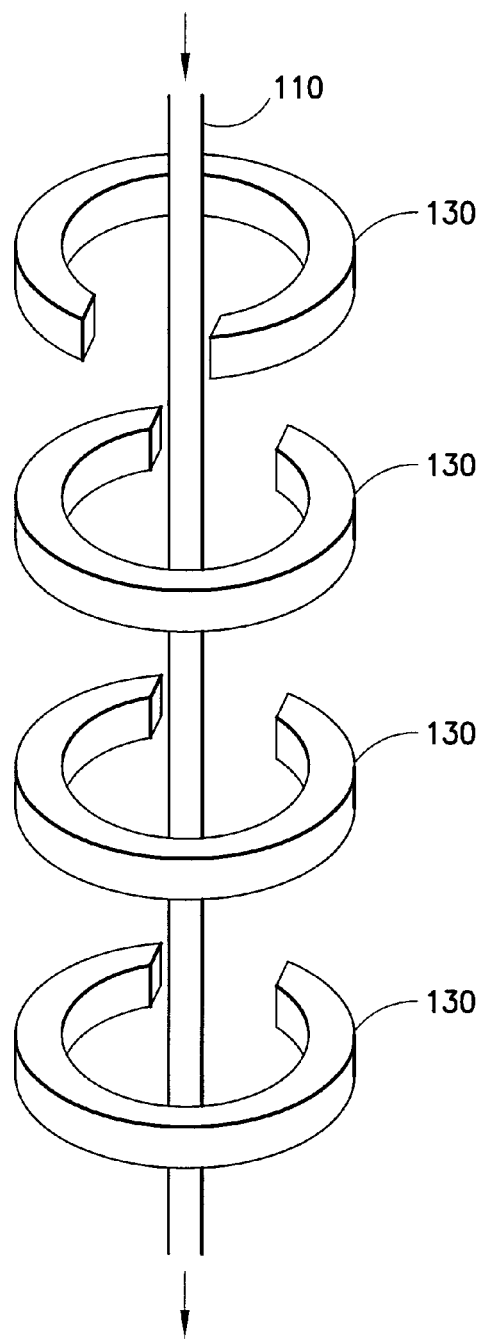
FIG. 10 shows the NMR device 100 optionally having the magnet 130 that is an array of magnets 130, the array of magnets are of a size larger than a size of the micro tube 110, according to embodiments of the disclosed subject matter.

FIG. 10 shows the NMR device 100 optionally having the magnet 130 that can be one or more magnets 130 or an array of magnets 130, the array of magnets 130 are of a size larger than a size of the micro tube 110. Further, the one or more magnets 130 can be micro magnets, wherein at least one magnet 130 can be a permanent magnet, a superconducting electromagnet, or a non-superconducting electromagnet.

Figure 11:
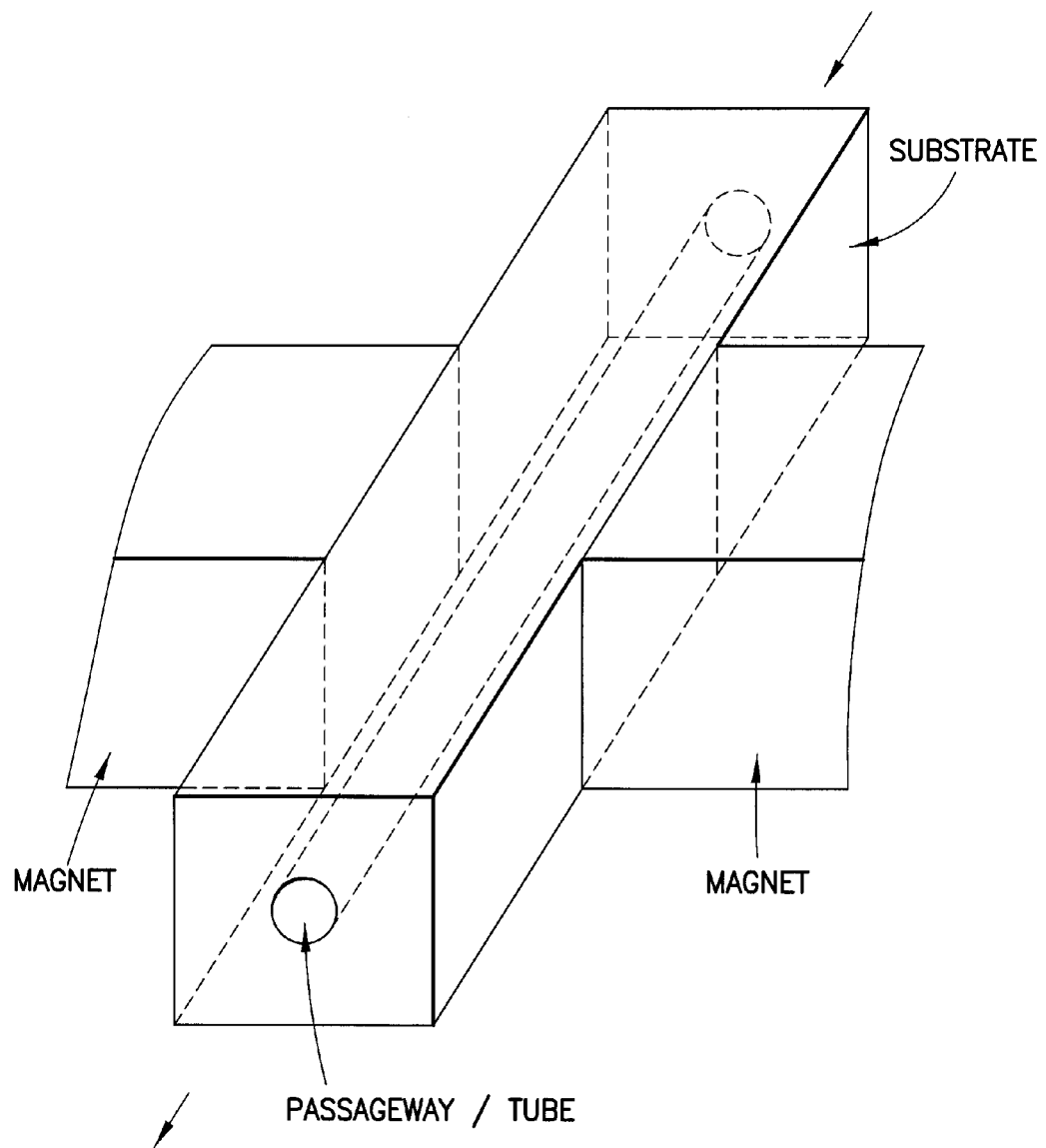
FIG. 11 shows the NMR device 100 optionally having the micro tube 110 comprising of a substrate having a passageway therethrough, as noted above in FIG. 3B, and the at least one magnet 130 can be disposed on the substrate, according to embodiments of the disclosed subject matter.

FIG. 11 shows the NMR device 100 optionally having the micro tube 110 comprising of a substrate having a passageway therethrough, as noted above and the at least one magnet 130 can be disposed on the substrate. Further, it is conceived that at least one magnet can be of a permeable magnetic material.

Figure 12:
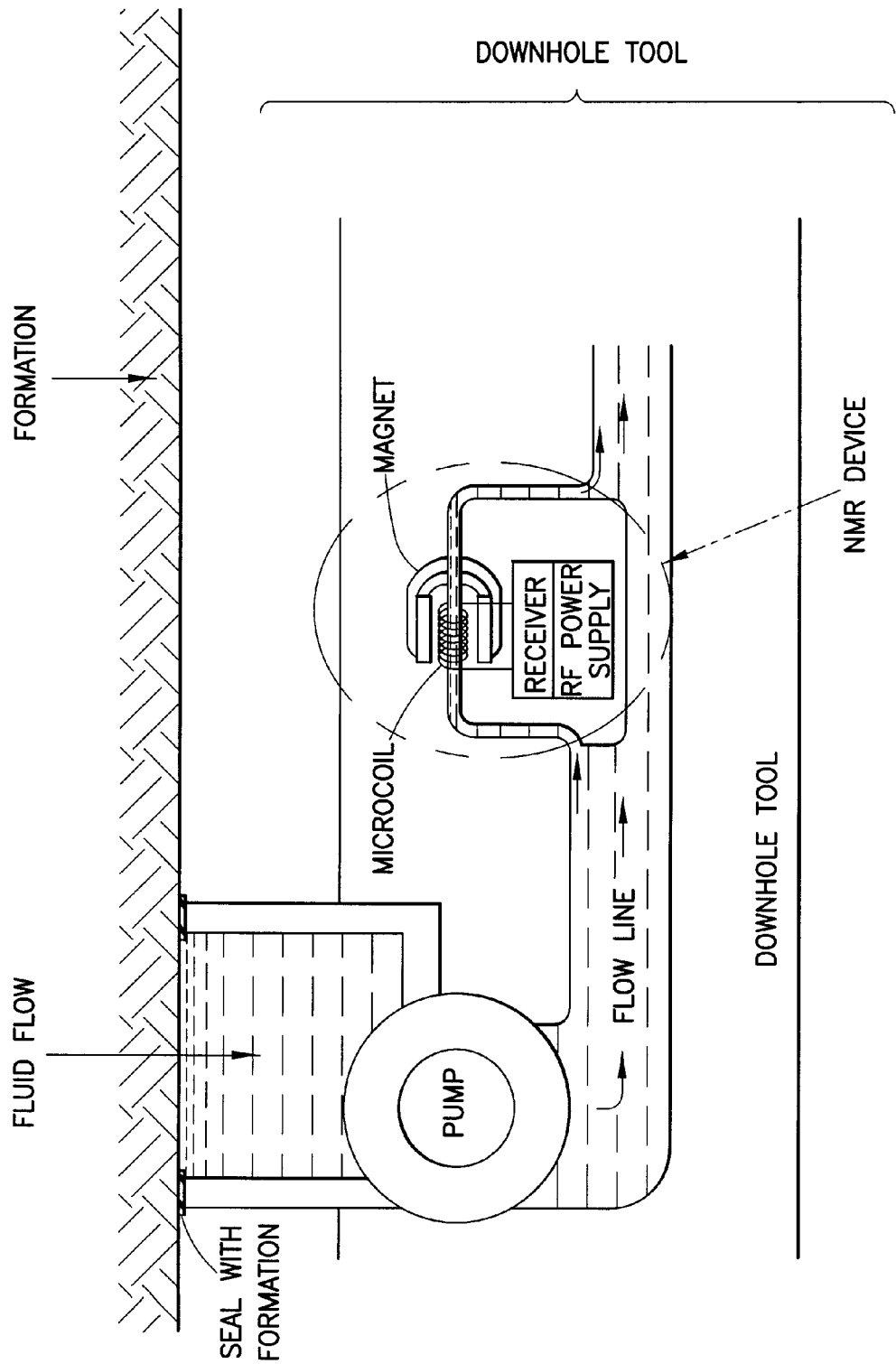
FIG. 12 shows the NMR device 100 in communication with the downhole tool along with a processor in communication with at least one receiver that can store the NMR measurement signals and analyzes the received NMR measurement signals to measure properties of the formation fluids based upon the micro NMR device 100 being powered by a power source having a power less than 1 mW or between 100 nW to 5 W, according to embodiments of the disclosed subject matter.

FIG. 12 shows the NMR device 100 in communication with the downhole tool along with a processor in communication with at least one receiver that can store the NMR measurement signals and analyzes the received NMR measurement signals to measure properties of the formation fluids based upon the micro NMR device 100 being powered by a power source having a power less than 1 mW or between 100 nW to 5 W. Other devices may be in communication with the NMR device 100 and downhole tool which may provide for data manipulation, data storage, further determination of fluid properties and characteristics and the like.

Figure 13:
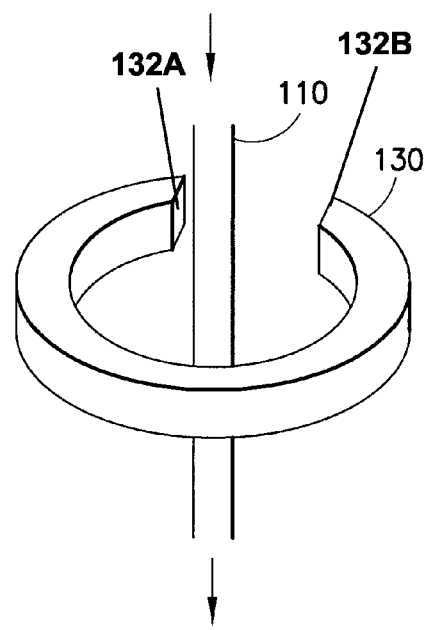
FIG. 13 shows the NMR device 100 optionally having the at least one magnet 130 including angled poles 134A and 134B that create a gradient of the applied magnetic field along a direction of flow (see arrows in FIG. 2) of the fluid in the micro tube 110 based upon the micro NMR device 100 being powered between 100 nW to 5 W, according to embodiments of the disclosed subject matter.

FIG. 13 shows the NMR device 100 optionally having the at least one magnet 130 including angled poles 132A and 132B that create a gradient of the applied magnetic field along a direction of flow (see arrows in FIG. 2) of the fluid in the micro tube 110 based upon the micro NMR device 100 being powered between 100 nW to 5 W. The use of the pole pieces in the magnet design can provide intrinsic internal gradient to provide diffusion measurement. The pole pieces can be interchanged so as to vary the gradient. The magnets can also be placed in series or parallel to have a suite of measurements to separate fluid types. The use of angled pole pieces can provide stability of the field to counter act temperate changes. It is noted that the size of the homogeneous gradient region must not be less than the maximum field shift due to the temperature change.

Still referring to FIG. 13, it is possible the at least one magnet 130 can be structured and arranged to provide for a homogeneous static field that allows for detection of NMR spectroscopy measurements based upon the micro NMR device 100 being powered between 100 nW to 5 W. Further still, the at least one magnet 130 can be structured and arranged to provide for a gradient field that allows for detection of NMR diffusion measurements based upon the micro NMR device 100 being powered between 100 nW to 5 W. It is also possible for at least one magnet 130 to have one of a single magnet or two or more magnets, that include one of a non uniform shaped or multiple non uniform shape pole pieces, that provide for at least two distinct regions of substantially different magnetic field strengths to allow detection of NMR measurements based upon the micro NMR device 100 being powered between 100 nW to 5 W.

Figure 14:
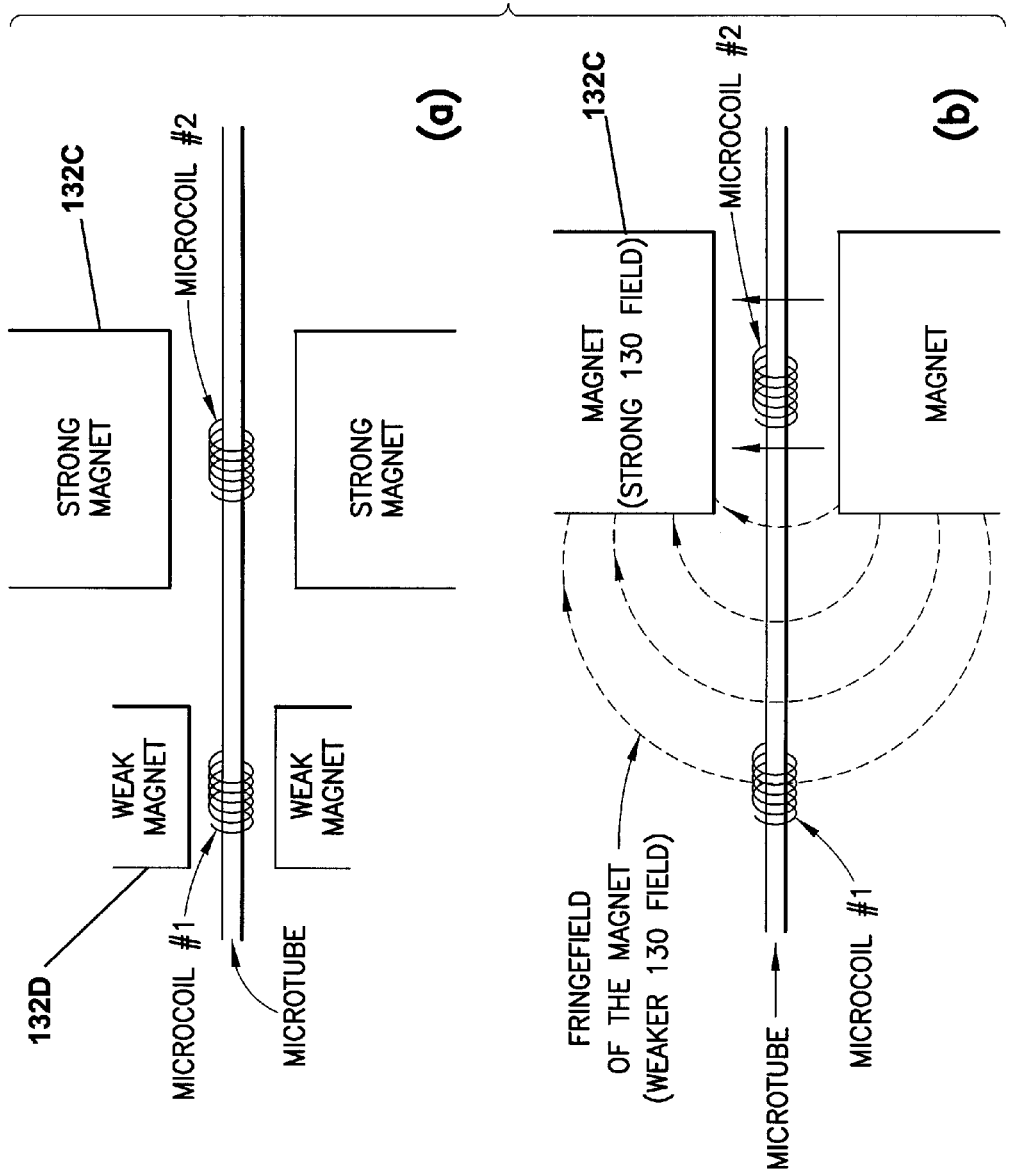
FIG. 14 shows the NMR device 100 optionally having the at least one magnet 130 including at least two magnets 132C and 132D that are arranged to provide for spatially separate-magnetic fields, each having substantially different magnetic field strengths, to allow detection of NMR asphaltene measurements based upon the micro NMR device 100 being powered between 100 nW to 5 W, according to embodiments of the disclosed subject matter.

FIG. 14 shows the NMR device 100 optionally having the at least one magnet 130 including at least two magnets 132C and 132D that are arranged to provide for spatially separate magnetic fields, each having substantially different magnetic field strengths, to allow detection of NMR asphaltene measurements based upon the micro NMR device 100 being powered between 100 nW to 5 W. In particular, it is possible to build a magnet system with varying fieldstrength, such as at least two spatially separated locations, where there is different coils tuned to the local resonant frequencies. Thus enabling multiple NMR measurements at different field and/or gradient strengths. This can be ideally suited for a flow line type of measurement in which multiple sensors (not necessarily NMR) can be used to make non-invasive measurement son the fluid sample.

Still referring to FIG. 14, the gradient strengths could be static or pulsed gradients that provide for the ability to obtain multiple diffusion measurements. These diffusion measurements may also be achieved through innovative pulse programs.

It is noted that analyzing the detected magnetic resonance signals includes extracting information about the fluid such as an NMR measurement. The NMR measurement can include, as noted above, a spectroscopy measurement, diffusion measurement, a relaxation measurement, an asphaltene measurement or a combination thereof.

Figure 15A:
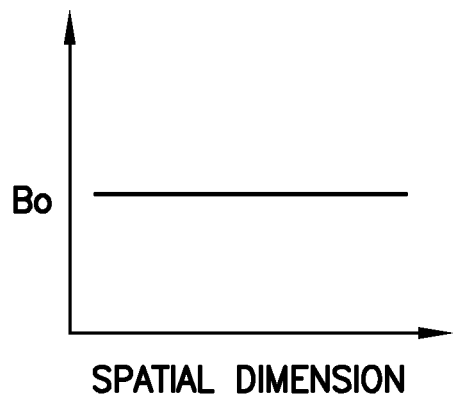
FIG. 15A to FIG. 15C depicts a cartoon sketch of three types of configurations of the external polarizing magnetic field Bo that could be used in different embodiments of the invention for different types of applications.
Figure 15B:
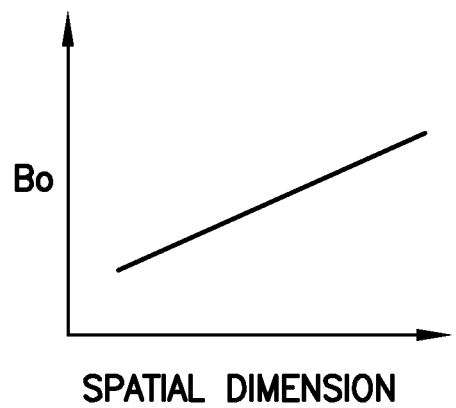
Figure 15C:
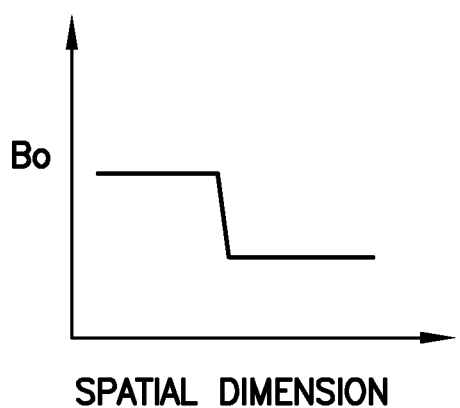

FIG. 15A to FIG. 15C depicts a cartoon sketch of three types of configurations of the external polarizing magnetic field Bo that could be used in different embodiments of the invention for different types of applications.

FIG. 15A depicts spectroscopy, with Bo having a high degree of spatial homogeneity;

FIG. 15B depicts diffusion measurements, where Bo needs to have a well-controlled gradual inhomogeneity, such as, typically, a uniform gradient that may be permanent or temporarily applied with electromagnetic coils; and FIG. 15C depicts relaxation dispersion measurements, where at least two regions of a field with substantially different magnitudes (factor of 2 or more) must be present. The fluid-conveying tube must extend along the spatial dimension indicated in the schematics.

According to embodiments of the disclosed subject matter, as noted above, it is possible the NMR measurement includes relaxation and diffusion measurements (either single or multi-dimensional as documented in the scientific literature); or spectroscopic measurements; or NMR dispersion measurements, i.e., measurements of relaxation properties as a function of the applied magnetic field. Each type of NMR measurements would have different requirements on the particulars of the magnet design, and the relative arrangement of the receiver RF coil and the magnet. Many such arrangements are possible accomplishing the same goal and the relative advantages and disadvantages certainly well noted. Spectroscopic measurements require high homogeneity of the magnetic field, on the order of parts-per-million over the volume of the sample. Thus, for spectroscopic measurement, the magnet would need to be designed to have a region of homogeneity as large as possible and the receiver coil or coils would need to be placed well inside that region. This is illustrated in panel (a) of the sketch above. The measurement of diffusion requires the presence of a field gradient, which could be permanent due to the magnetic material present in the magnet itself, or externally applied with separate conducting gradient coils. Many different designs of magnetic gradient systems can be considered, but the concept of the disclosed subject matter is illustrated in panel (b) of the sketch above. The RF coil or coils should be place inside the region with the gradient. Finally, the measurement of relaxation dispersion requires the presence of regions of magnetic field with substantially different magnitudes. This could be accomplished by having the fluid-conveying tube go through regions containing more or less magnetic material and having the RF detection coils placed in those regions and tuned to the appropriate local Larmor frequency corresponding to the field at that spatial location. At least two such regions and coils are necessary in order to accomplish a measurement of dispersion, while more coils placed at a wider range of field strengths would provide a better mapping of the fluid dispersion. The schematic is given in panel (c) of the sketch. Again, there are many possible ways of arranging the magnetic material in order to create regions of different magnetic field. The simplest such arrangement would be to have one RF coil placed inside the bore of the magnet, or more generally, inside the region of strong homogeneous field of the magnet, while placing the other RF coils around the fluid-conveying tube, incrementally further and further away from the magnet, with the result of weakening magnetic field with the distance. However, to emphasize, many other designs resulting in substantially variable fields, with coils tuned to the corresponding frequencies would accomplish the task.

Regarding the diffusion measurement, information on hydrocarbon chain length distributions can be obtained using the diffusion spectrum that is measured by the device. It is noted that the subject matter disclosed incorporates the aspect of providing NMR bulk and spectroscopic measurements while down an oil well at elevated pressure and temperate. On aspect of the disclosed subject matter is to provide detailed fluid analysis of oils to determine fluid characteristics and "finger printing" of the oil samples. This can aid in the determination of compartmentalization in reservoirs. Further, T1, T2 and diffusion measurement on oils and oil/water emulsions can be accomplished using the NMR device, which can provide multi-dimensional data (2D, 3D, 4D, etc.).

Regarding asphaltene measurements, asphaltenes can be considered the heaviest fraction of crude oil. They crucially affect oil production at all stages due to their instability under environmental changes (temperature, pressure, dilution by solvents, etc) which causes them to precipitate out, clogging the formation as well as transport pipelines. Qualitatively, their presence increases the T1 and T2 relaxation of the remaining crude molecules (or the so-called maltene) while leaving their diffusion largely unaffected, resulting in a characteristic near-vertical shape of the D-T2 map. To obtain quantitative information about the amount of asphaltenes present as well as about their aggregation properties, various models can be used to relate the size of their clusters to the changes in NMR relaxation. All these models inevitably include dependence on the Larmor frequency (or the strength of the polarizing magnetic field) since the asphaltene-induced relaxation fundamentally derives from the slowed mobility in the vicinity of an asphaltene macromolecule, and the effect of slower correlation times will depend on the observation frequency. Field cycling, i.e., rapid switching of the polarizing field in order to scan the Larmor frequencies, is a common technique used for aggregation measurements. It would be extremely challenging to implement downhole, due to the high power requirements and the complexity of the switching electronics. The disclosed subject matter herein circumvents the challenges of rapid field switching by proposing to place separate microcoils, each tuned to different Larmor frequency, at different locations with respect to the permanent polarizing magnet. As the fluid flows from one coil to the next, measurements at different fields can be performed, thus providing information necessary for asphaltene cluster size determination. Thus, T1, T2, D-T2 and T1/T2 ratio measurements can be made to obtain information on the presence and quantity of Asphaltene in oil.

According to embodiments of the disclosed subject matter, it is contemplated that a NMR system can be embedded into a microfluidic system. This module can be designed to fit into downhole fluid sampling tool(s) such as, but not limited to, downhole tool. This module can be capable of providing NMR data on oil flowing through the fluid sampling tool. This microcoil can provide downhole NMR measurements on pure oil samples and provide fluid characterization of the sample in real time.

At least one operational sequence of at least one method of the disclosed subject matter includes after fluid passes through the separator membrane, the oil flows down the capillary tube through the NMR micro coil. Then, the measurements on T1, T2 and diffusion can be made. It is possible that other types of measurement can be made such as determining true fluid and formation properties, hydrogen Index (HI) which can be used to calibrate other logs.

The NMR micro coil can be operated in continuous mode, or it can be triggered to run when a particular fluid is passing through, at the discretions of the operator at the surface. There will be a telemetry link to the surface to provide real time information. They may also be run as memory tools where there data is stored on a HDD downhole and then processed when the tool is brought to the surface. The power can either be from a battery stored in the tool or from the main tool power lines in the logging tools, as noted above.

Other methods are conceived such as prepolarizing the fluid prior to the fluid entering the micro tube. Further, since the NMR device can be a micro NMR device multiple NMR devices can be used in one application, wherein the application may be structured to obtain multiple NMR measurements. The gathered NMR measurements could all be in real time so as to provide multiple end-result data or analyzed data results that are either redundant or sequenced over a period of time.

Further, while the present disclosed subject matter has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present disclosed subject matter in its aspects. Although the present disclosed subject matter has been described herein with reference to particular means, materials and embodiments, the present disclosed subject matter is not intended to be limited to the particulars disclosed herein; rather, the present disclosed subject matter extends to all functionally equivalent structures, methods and uses, such as are within the scope of the appended claims.

What is claimed is:

1. A downhole tool for a fluid, the downhole tool comprising:
    a nuclear magnetic resonance (NMR) device that comprises:
        a micro tube for containing the fluid;
        at least one magnet configured to apply a static magnetic field to at least a portion of the fluid within the micro tube, wherein the at least one magnet comprises at least two magnets that each apply different magnetic field strengths along the micro tube; and
        at least one coil coupled to a tuning circuit and configured to apply radio frequency (RF) pulses to the portion of the fluid within the micro tube, wherein the coil and circuit are tuned to a Larmor frequency that corresponds to the static magnetic field applied by the at least one magnet.

2. The downhole tool of claim 1, wherein at least one magnet includes angled poles that create a gradient within the applied magnetic field, wherein the gradient is in a direction of fluid flow within the micro tube.

3. The downhole tool of claim 1, wherein at least one magnet is configured to apply a homogeneous static magnetic field.

4. The downhole tool of claim 1, wherein at least one magnet is configured to apply a static magnetic field with at least two distinct regions of substantially different magnetic field strengths.

5. The downhole tool of claim 1, wherein the NMR device is a NMR probe that is controlled by a spectrometer and powered by a power supply.

6. The downhole tool of claim 1, wherein the power used to power the NMR device is less than 75 mW.

7. The downhole tool of claim 1, wherein the at least one coil comprises a metal or a metal alloy.

8. The downhole tool of claim 1, wherein the tuning circuit includes a capacitor and an inductor.

9. The downhole tool of claim 1, wherein the at least one coil comprises at least two coils, wherein each coil is configured to apply RF pulses at spatially separate locations along the micro tube and each coil is tuned to a different Larmor frequency.

10. The downhole tool of claim 9, wherein electrical inductances of the at least two coils are decoupled from each other.

11. The downhole tool of claim 1, wherein the static magnetic field strength is between 0.1 to 2 T.

12. The downhole tool of claim 1, wherein the NMR device comprises one or more coil shielding devices.

13. The downhole tool of claim 1, wherein the at least one coil is a solenoid-shaped coil encompassing a volume along the micro tube.

14. The downhole tool of claim 1, wherein the at least one coil is fabricated on the micro tube.

15. The downhole tool of claim 1, wherein the at least one coil is spiral and substantially planar.

16. The downhole tool of claim 8, wherein the capacitor comprises a variable capacitor.

17. The downhole tool of claim 1, wherein the micro tube has a diameter from 100 microns to 5 millimeters.

18. The downhole tool of claim 1, wherein the micro tube has a length of less than 50 mm.

19. The downhole tool of claim 1, wherein the micro tube comprises a capillary tube.

20. The downhole tool of claim 1, wherein the micro tube comprises a substrate that defines a channel.

21. The downhole tool of claim 20, wherein the substrate comprises at least two pieces that are attached together to form the channel.

22. The downhole tool of claim 20, wherein the substrate comprises an electrically insulating material.

23. The downhole tool of claim 1, further comprising a fluid delivery system in fluid communication with the micro tube.

24. The downhole tool of claim 1, wherein at least one magnet is an array of magnets.

25. The downhole tool of claim 1, wherein at least one magnet is a permanent magnet.

26. The downhole tool of claim 1, wherein the micro tube comprises a substrate that defines a channel and the at least one magnet is disposed on the substrate.

27. The downhole tool of claim 1, wherein at least one magnet comprises a permeable magnetic material.

28. The downhole tool of claim 1, wherein at least a portion of the NMR device is constructed using a substrate and micro fabrication techniques.

29. The downhole micro NMR device of claim 1, wherein the downhole tool comprises a downhole fluid sampling tool.

30. A method for making a downhole nuclear magnetic resonance (NMR) measurement of a fluid using a NMR device, the method comprising:
flowing the fluid into a micro tube of the NMR device;
applying a static magnetic field to at least a portion of the fluid within the micro tube;
wherein applying the static magnetic field comprises applying to the fluid two spatially separate static magnetic fields having different magnetic field strengths;
applying radio frequency (RF) pulses to the portion of the fluid within the micro tube;
detecting magnetic resonance signals generated within the fluid; and
analyzing the detected magnetic resonance signals to extract information about the fluid.

31. The downhole method of claim 30, wherein the applied static magnetic field comprises a homogeneous static field.

32. The downhole method of claim 30, wherein the applied static magnetic field comprises a gradient static field.

33. The downhole method of claim 30, wherein the static magnetic field includes at least two distinct regions of substantially different magnetic field strengths.

34. The downhole method of claim 30, wherein the NMR device is powered by less than 1 mW.

35. The downhole method of claim 30, wherein the RF pulses are applied at spatially separate locations along the micro tube and each of the RF pulses, at spatially separate locations, are applied at different Larmor frequencies.

* * * * *